(12) United States Patent
Wexler (10) Patent No.: US 8,202,253 B1
(45) Date of Patent: Jun. 19, 2012

(54) METHOD AND APPARATUS FOR INTRODUCING AN INTRAVENOUS CATHETER

(76) Inventor: Toby J. Wexler, Lafayette, LA (US)

(*) Notice: Subject to any disclaimer, the term of this patent is extended or adjusted under 35 U.S.C. 154(b) by 395 days.

(21) Appl. No.: 12/288,282

(22) Filed: Oct. 17, 2008

(51) Int. Cl.
A61M 5/178 (2006.01)

(52) U.S. Cl. ......... 604/168.01; 604/164.01; 604/164.02; 604/164.09; 604/164.13; 604/161

(58) Field of Classification Search ............. 604/191, 604/162, 192, 167.03, 164, 164.02, 164.01
See application file for complete search history.

(56) References Cited

U.S. PATENT DOCUMENTS

| | | | | |
|---|---|---|---|---|
| 3,859,998 A | * | 1/1975 | Thomas et al. | 604/168.01 |
| 4,966,589 A | | 10/1990 | Kaufman | |
| 5,000,740 A | * | 3/1991 | Ducharme et al. | 604/162 |
| 5,242,414 A | * | 9/1993 | Fischell et al. | 604/168.01 |
| 5,279,572 A | | 1/1994 | Hokama | |
| 5,520,657 A | * | 5/1996 | Sellers et al. | 604/191 |
| 5,531,701 A | | 7/1996 | Luther | |
| 5,575,777 A | * | 11/1996 | Cover et al. | 604/198 |
| 6,156,010 A | | 12/2000 | Kuracina et al. | |
| 6,213,978 B1 | | 4/2001 | Voyten | |
| 7,125,396 B2 | | 10/2006 | Leinsing et al. | |
| 2004/0106903 A1 | * | 6/2004 | Shue et al. | 604/168.01 |
| 2005/0131350 A1 | * | 6/2005 | Shaw et al. | 604/168.01 |

* cited by examiner

*Primary Examiner* — Kevin C Sirmons
*Assistant Examiner* — Bradley Thomas, Jr.
(74) *Attorney, Agent, or Firm* — Garvey, Smith, Nehrbass & North, L.L.C.; Gregory C. Smith; Julia M. FitzPatrick (57) ABSTRACT

A catheter insertion apparatus with visual indication of needle penetration of a blood vessel and placement of the catheter cannula within the blood vessel, using blood vessel pressure to indicate needle penetration by the presence of blood within a transparent chamber within the apparatus and the displacement of a plunger to create a negative pressure on the cannula and thus allowing blood to be visible within the catheter hub thereby indicating the introduction of the cannula into the blood vessel.

18 Claims, 10 Drawing Sheets

METHOD AND APPARATUS FOR INTRODUCING AN INTRAVENOUS CATHETER

1. FIELD OF THE INVENTION

The present invention relates generally to methods and apparatus for introducing a peripheral Intravenous (I.V.) catheter into a subcutaneous blood vessel, and more particularly to an apparatus and method for inserting a cannula into a blood vessel using an insertion apparatus having suction capability for providing a visual indication of the positive placement of the cannula within a blood vessel.

2. GENERAL BACKGROUND

It is a well known, and the established practice, for inserting a catheter into subcutaneous blood vessels, to use a cannula and needle assembly for starting an I.V., thereby establishing a continuous medication injection site or venipuncture site to withdraw blood from the blood vessel. Such procedures commonly use an over the cannula needle process whereby a hollow bore needle resides within the cannula hub and which also extends slightly beyond the end of the flexible cannula. The cannula may also be introduced by way of a solid Trocar when there is no need to introduce a medication, or where flashback of arterial blood or fluid is not needed. However, in either case, once the stylet (the needle or Trocar) punctures the blood vessel, the cannula is then deployed forward and off of the end of the needle or Trocar, thereby threading the cannula into the lumen of the vessel. The needle or Trocar is then removed, thereby leaving the cannula threaded within the blood vessel. In either case the needle or Trocar is used to penetrate the subcutaneous layers of the skin and puncture the selected blood vessel and thereby allow insertion of the flexible cannula portion of the catheter assembly to enter the blood vessel. The needle or Trocar must pierce the blood vessel and be at a precise angle of between 20-30 degrees so as to allow the cannula to proceed along the longitudinal bore of the blood vessel. Several factors complicate the successful placement of I.V. catheters. For example, the inherent instability of blood vessels often makes them very difficult to pierce. Furthermore, the needle or Trocar may miss the blood vessel completely, pass through the blood vessel, or the needle or Trocar may enter the blood vessel but the cannula fails to make penetration when the practitioner attempts to deploy the cannula. Frequently, poor cannula placement causes the cannula to be expelled or displaced from the blood vessel by movement of the cannula hub while anchoring the cannula assemble to the patient, or attempting to use the cannula to administer fluid therapy.

A visual indication of needle penetration of the blood vessel is currently achieved by what is known as backflow or flashback of blood into the hub portion of the insertion apparatus. This is a result of blood passing through the needle under arterial pressure into the catheter hub, thus providing a visual indication that penetration of the blood vessel has occurred and that blood is present in the vicinity of the needle. However, this is not an indication that the blood vessel has been penetrated properly or that the cannula tip has fully penetrated the lumen of the blood vessel.

If the practitioner deploys the cannula without proper placement the vein is blown, creating a subcutaneous hematoma around the site. It then becomes very difficult to reacquire the blood vessel because a clot often forms in and around the blood vessel, which prohibits further flashback into the flashback chamber already filled with blood. The practitioner then needs a suction apparatus to withdraw venous blood and possibly reacquire the blood vessel. For this reason it is common for the nurse to place a syringe on the end of the catheter apparatus to provide this suction. This suction helps to relocate the vein because when the needle penetrates a blood vessel, blood can be withdrawn into the syringe. Many inventions are described to reproduce this procedure. Unfortunately, as has been explained, blood withdrawn through the needle only serves to verify that the needle is within the blood vessel. This procedure places the practitioner at the same shortcoming common to all catheters. Locating the vein is only half the problem. Threading the cannula within the lumen of the blood vessel is the current challenge. If the cannula is not well within the lumen of the vessel it will deflect off the vessel wall and blow the vein. Difficulty placing the cannula has also resulted in the use of butterfly catheters which do not use a cannula, but instead leave only a sharp needle within the vessel. Unfortunately, except in very short term use, these will cause trauma to the vein if any movement occurs at the puncture site. Therefore, it would be advantageous to create a suction or negative pressure on the cannula at the most critical location, around the exterior of the needle at the cannula tip, and provide a visual indication of the fact that the cannula is threaded within the blood vessel prior to deploying the cannula and removing the stylet. This would not only facilitate locating the vein, but provide a greater degree of success at actually threading the cannula into the vein once located.

In many cases, using existing technology, the needle derives backflow but has actually passed completely though the selected blood vessel. When the cannula is subsequently deployed, subcutaneous hemorrhage occurs resulting in a large swelling at the site of the venipuncture. Swelling prohibits reacquiring the vein for any further attempts at placing a catheter. This problem frequently occurs when the practitioner is trying to find a vein and actually has the needle in the vein but does not know it due to failure to get a positive flashback in the catheter flash back chamber. The practitioner often attempts to reposition the needle repeatedly searching for the vein. In doing so she actually punctures the vessel, (once or numerous times) with the stylet. Then instead of sliding the catheter cannula off of the needle and into the vein, the practitioner pulls the needle and cannula out of the vein and continues searching. This is a very frequent malfunction of the current catheter assemblies because they rely on blood pressure to give flashback. However, blood pressure can be weak due to many common conditions, such as small veins, dehydration, sclerosis of the vein from prior venipuncture, or medical conditions. Under perfect conditions a blown vein does not occur because, when the needle punctures the vein, the positive flashback demonstrates to the practitioner that the cannula should be deployed so as to allow the cannula to seal the hole made by the needle. The needle is then removed and discarded, leaving the cannula in the vein.

Missed attempts to pierce a blood vessel and thereby establish a catheter infusion site result in the need to dispose of the catheter set, composed of a cannula and hub assembly, and a syringe and needle or Trocar, secure the wound site, and seek a new site starting over with a fresh catheter set.

Attempts to improve the procedure by utilizing a cannula visual indicator provides a transparent cannula and a grooved needle to allow the passage of blood along the length of the needle between cannula and the needle. However, backflow can still occur along the needle due to capillary flow and thus be mistaken as arterial flow through the cannula. In other cases and most often the needle has passed clear through the vessel, thus producing a false indication of cannula insertion.

It is therefore, an object of the present invention to provide a cannula insertion apparatus having visual means for indicating arterial pressure and a means for positive indication of cannula placement within a blood vessel using a vacuum to draw blood from the blood vessel through the annulus between the needle and cannula and into a cavity located within the insertion apparatus.

It is another object of the invention to provide a more reliable, less expensive and more ergonomically correct cannula insertion apparatus.

Yet another object of the invention is to provide a cannula insertion device capable of redeployment of the needle and cannula during insertion if it becomes obvious that the cannula is misplaced without the need to withdraw the catheter assembly, dispose of the assembly, and relocate to a new site.

3. SUMMARY OF THE INVENTION

A method and apparatus for the introduction of a peripheral Intravenous (I.V.) catheter disclosed herein utilizes an introducer which is a relatively short ergonomically shaped tubular member that fits readily between the user's thumb and forefinger and that is adaptive to a cannula and hub assembly, for inserting the cannula into a selected subcutaneous blood vessel and includes a visual indication of the proper placement of the cannula. The introducer includes a removable plunger and stem portion with a needle extending from the plunger, which is slidable within the tubular member and in fluid communication with a cavity located within the plunger stem and vented to the atmosphere. When a blood vessel is pierced, by the needle, arterial pressure allows blood to flow though the needle and into the cavity located within the stem.

The stem portion further includes a knob for withdrawing the plunger, thereby retracting the plunger and its attached needle a short distance from within the cannula. Retraction of the plunger forms a vacuum in the annulus between the needle and cannula, thereby drawing blood from a blood vessel or fluid from an anatomical space into the cavity created by displacement of the plunger within the tubular member, thereby indicating a proper placement of the cannula within the blood vessel or space. If no blood is retracted into the tubular member, the plunger is compressed and the entire assembly may then be extended or repositioned and the plunger can again be retracted until blood becomes visible within the tubular member. When blood is visible within the plunger chamber, the cannula can then be deployed, thus moving the cannula farther into the lumen of the blood vessel. The plunger and needle can then be withdrawn from within the transparent tubular member. It is also envisioned that the tubular member, may be fitted with a self healing barrier for passing medication via a syringe needle or be provided with a twist type coupling for attaching a hose or the like for continuous medications.

4. BRIEF DESCRIPTION OF THE DRAWINGS

For a further understanding of the nature and objects of the present invention, reference should be made to the following detailed description taken in conjunction with the accompanying drawings, in which, like parts are given like reference numerals, and wherein.

5. DETAILED DESCRIPTION OF THE PREFERRED EMBODIMENT

Figure 1:
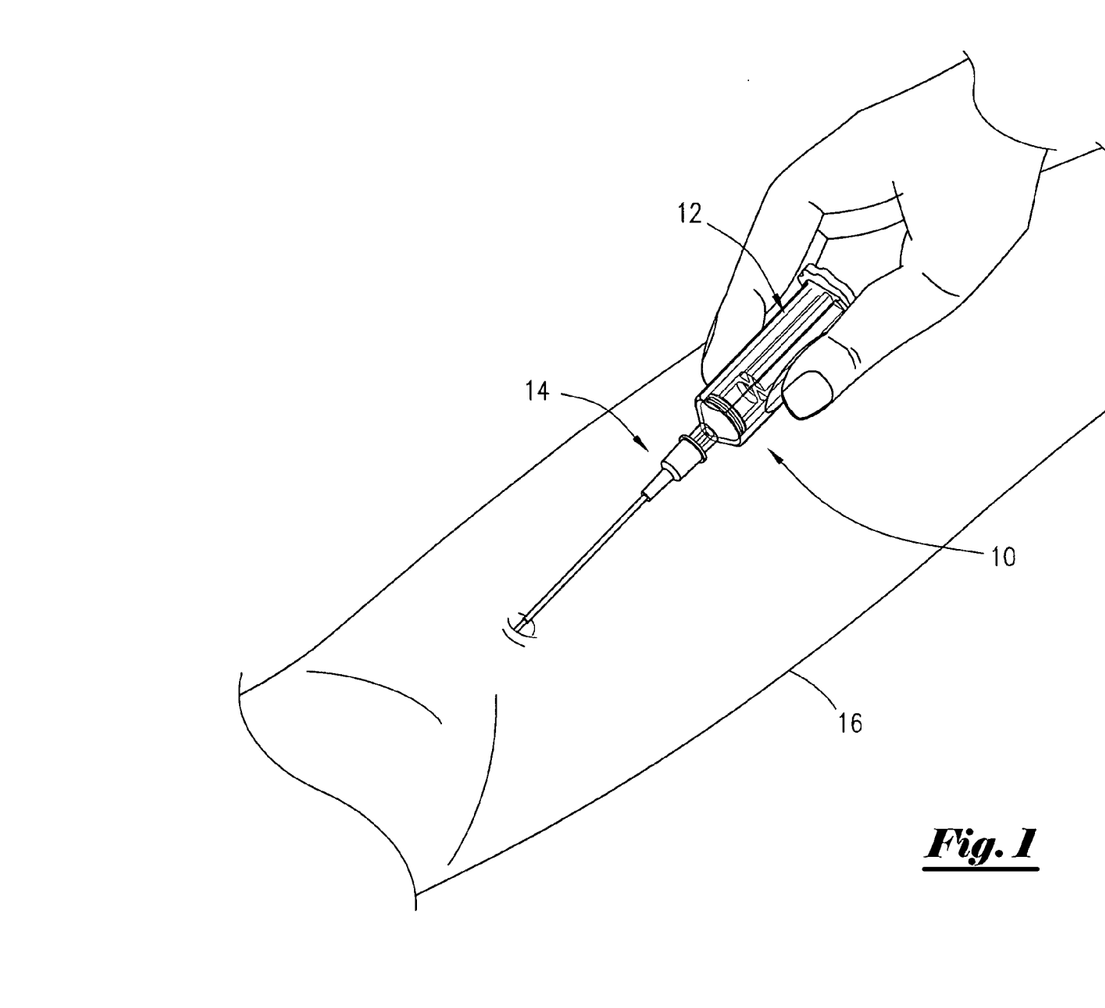
FIG. 1 is an isometric view of the venous catheter insertion apparatus in use.
Figure 2:
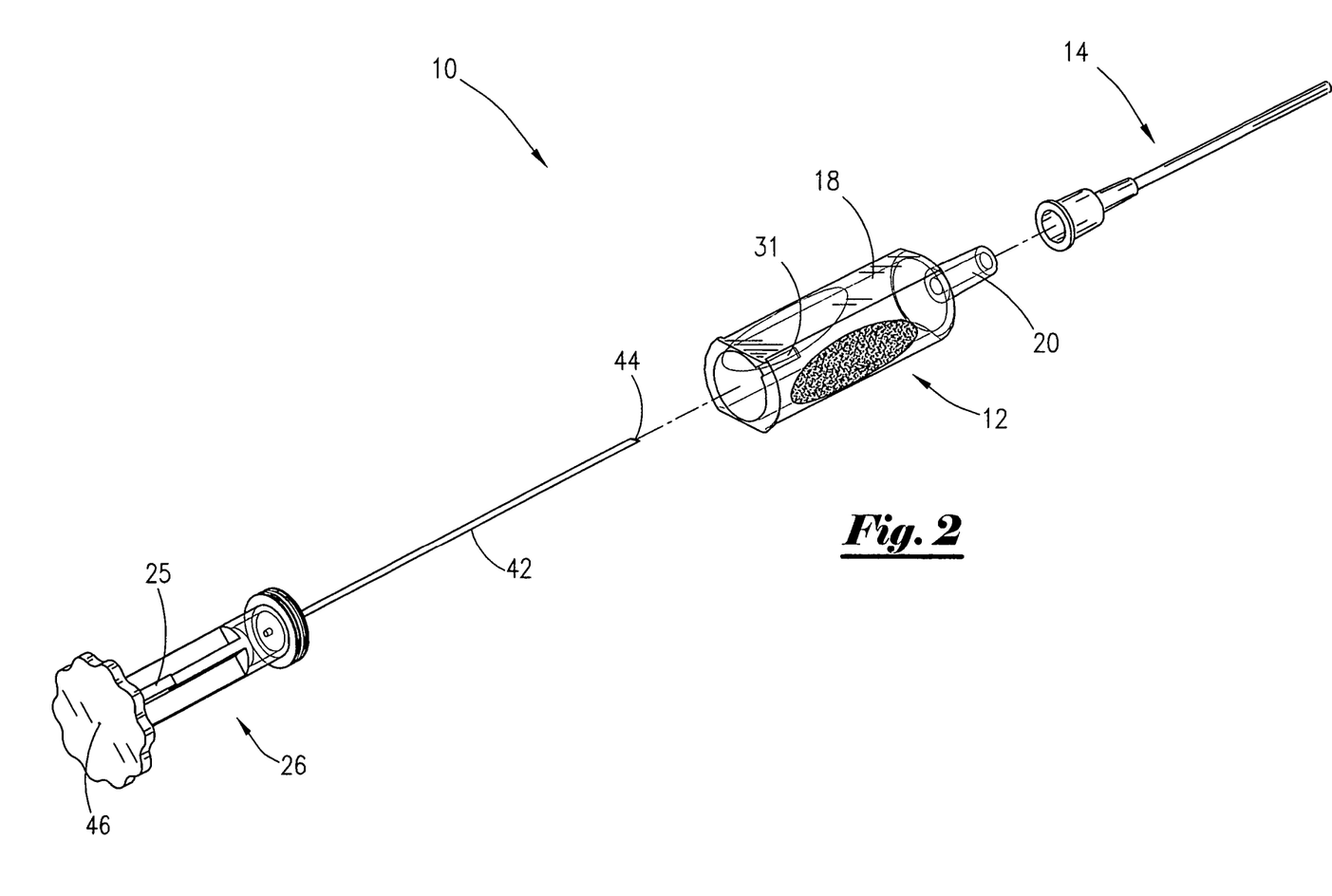
FIG. 2 is an exploded view of the apparatus.

As shown in FIG. 1, a practitioner is using a new catheter insertion apparatus 10 to insert the catheter assembly 14 into a patient's arm 16. The insertion assembly 12, in addition to the catheter assembly 14, includes a transparent sleeve 18 and plunger assembly 26 as shown in FIG. 2. As further seen in FIG. 3, the transparent sleeve 18 is a transparent elongated tubular member open at each end with a nipple portion 20 at one end. The nipple portion 20 is tapered to fit within the hub member 54 of the catheter assembly 14 to which the cannula 52 is attached, therefore practically any catheter of the proper size and length made for use with a syringe may be used with the new insertion assembly 12.

Figure 3:
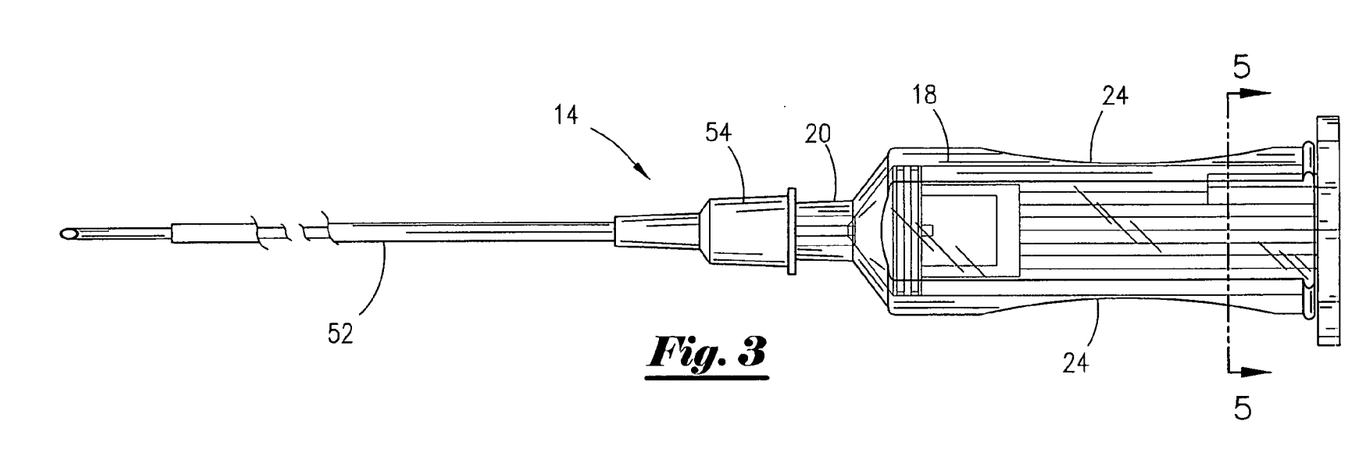
FIG. 3 is a top view of the apparatus.
Figure 4:
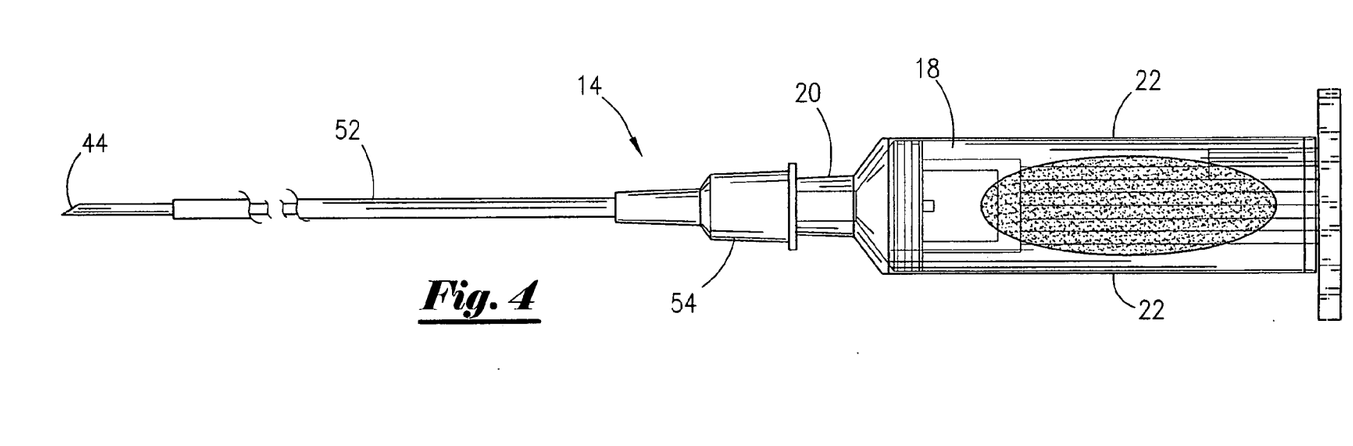
FIG. 4 is a side elevation view of the apparatus.

As further seen in FIG. 3 and FIG. 4, the exterior of the transparent tubular transparent sleeve 18 includes flat areas 22 on both upper and lower sides as well as concaved shaped sides 24 provided with embossing to assist in gripping the transparent sleeve 18 using only the practitioner's thumb and forefinger. The insertion assembly 12 further includes an elongated plunger assembly 26 slidable within the transparent sleeve 18. The plunger assembly is provided with a disk or knob 28 at one end for displacing the plunger within the transparent sleeve 18.

Figure 5:
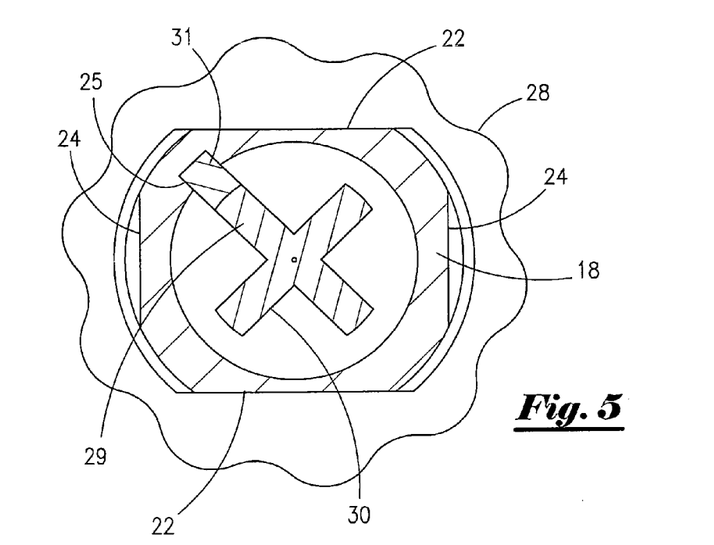
FIG. 5 is a cross-section view of the apparatus taken along site line 5-5 as seen in FIG. 3.
Figure 7:
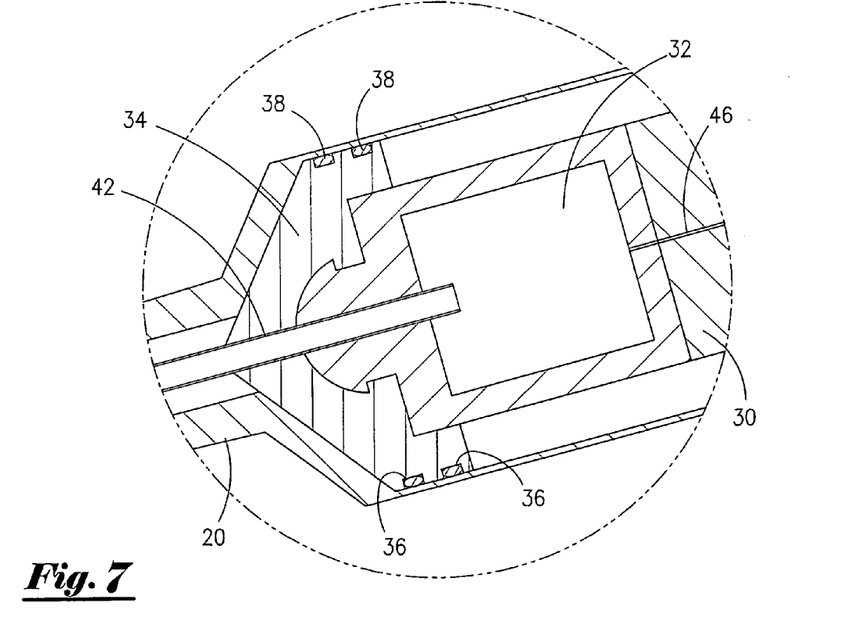
FIG. 7 is a partial section-view of area 7 as seen in FIG. 6.

The plunger assembly 26 also includes a stem portion 30 forming a cross when seen in cross-section as shown in FIG. 5. One leg 29 of the stem portion 30 includes a step portion 25 located adjacent the knob 28. In addition, a corresponding notch 31 is provided within the transparent sleeve 18 to accept the step portion 25 of the leg 29 to insure orientation of the plunger assembly 26 relative to the transparent sleeve 18 so as to insure proper orientation of the beveled portion of the needle discussed hereafter. Stem portion 30 is attached to a transparent chamber 32, seen in FIG. 7. The plunger assembly 26 further includes a needle base 34 of a hard bonded material attached to the transparent chamber 32 and includes o-ring grooves 36 fitted with o-rings seals 38 thereby producing a sliding seal between the plunger assembly 26 and interior of the transparent sleeve 18. The needle base 34 is also cone shaped on one side and is cooperative with the shape and size of the internal funnel shape of the interior of the nipple portion 20 of the transparent sleeve 18.

Plunger assembly 26 also includes the elongated tubular needle 42, seen in FIG. 2 having a beveled tip 44 at the distal end with the opposite end centrally located and fixed within the embedding or needle base member 34, so as to allow a viscous fluid such as blood to pass through the needle 42 and into the transparent chamber 32. The chamber 32 is provided with an opening to atmosphere through the stem portion 30 via a vent port 46.

The beveled tip of the needle 44 is oriented relative to the plunger 26 and transparent sleeve 18 so that the bevel is always facing upwards due to a notch 31 located with the wall of transparent sleeve 18 and a cooperative step portion 25 of the leg 29 of the stem 30.

Catheter insertion apparatus 10 is fitted with a catheter assembly 14 that includes a cannula 52 and a hub 54 conforming to the exterior portion of the nipple portion 20 of the transparent sleeve 18. The cannula 52 is sized according to the diameter and length of the needle 42 and may be provide separately or in combination with the insertion apparatus 12.

Figure 6:
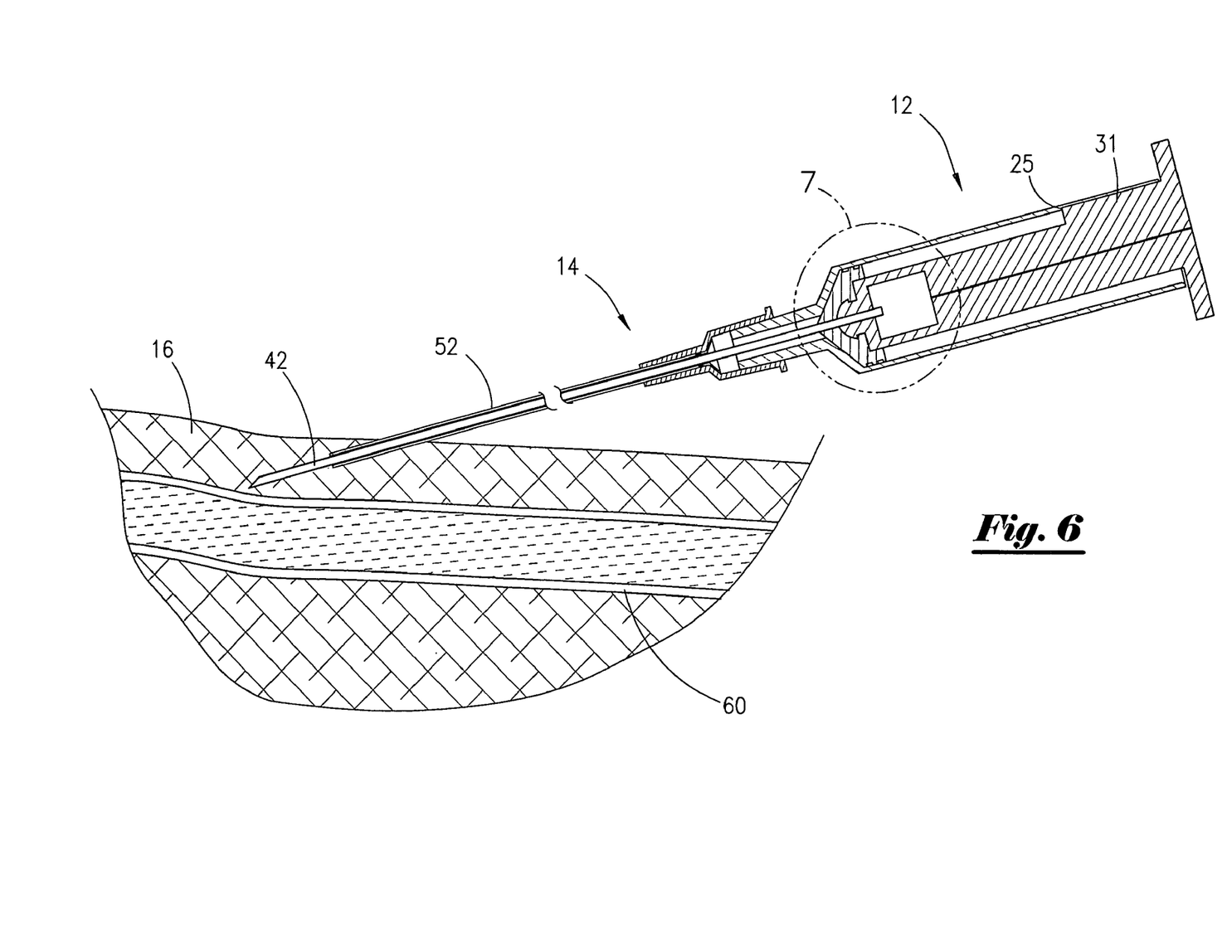
FIG. 6 is a cross-section view of the apparatus and partial view of subcutaneous blood vessel.
Figure 8:
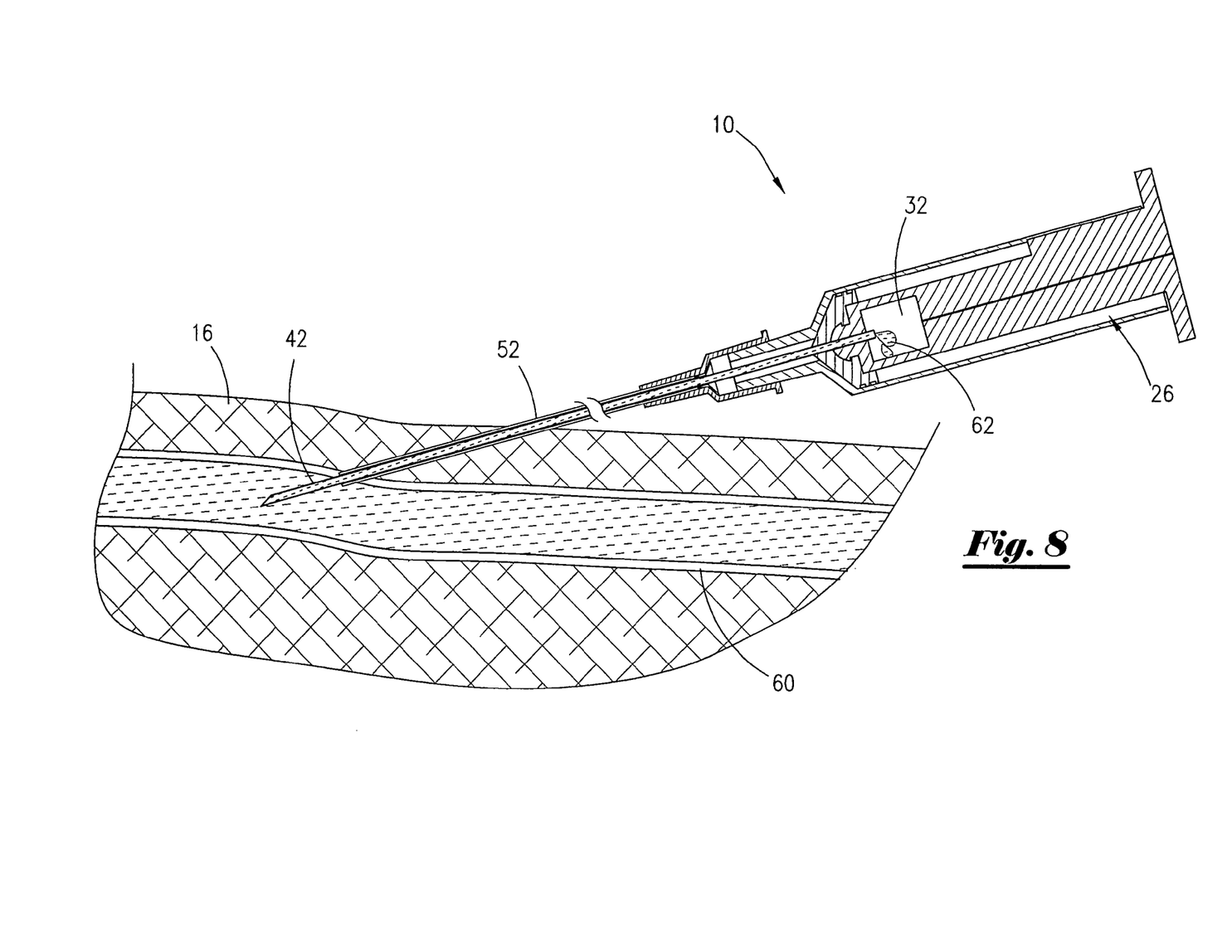
FIG. 8 is a cross-section view of the apparatus and partial view of subcutaneous blood vessel showing needle penetration of the blood vessel.
Figure 9:
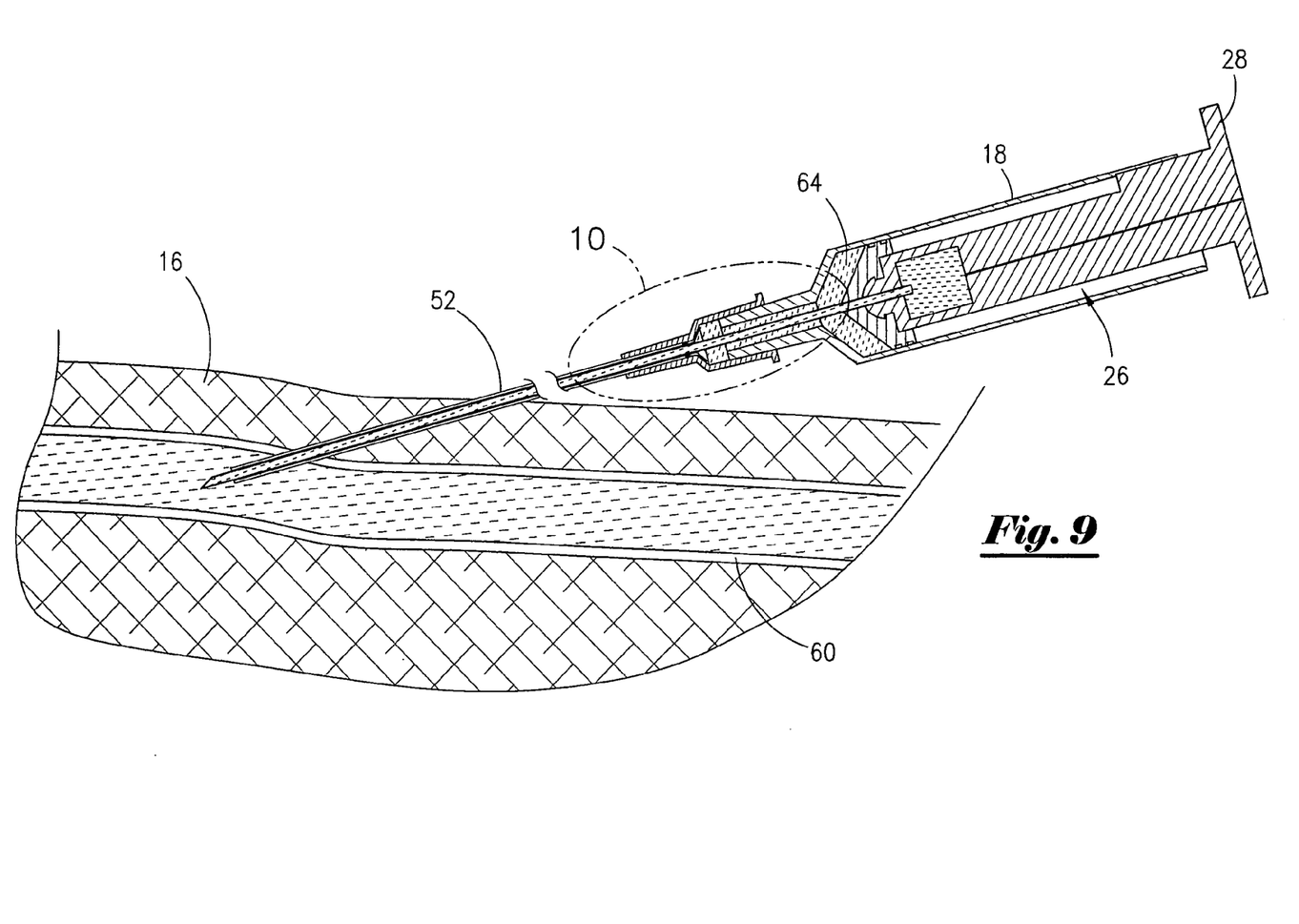
FIG. 9 is a cross-section view of the apparatus and partial view of subcutaneous blood vessel showing needle penetration and cannula insertion of the blood vessel.
Figure 10:
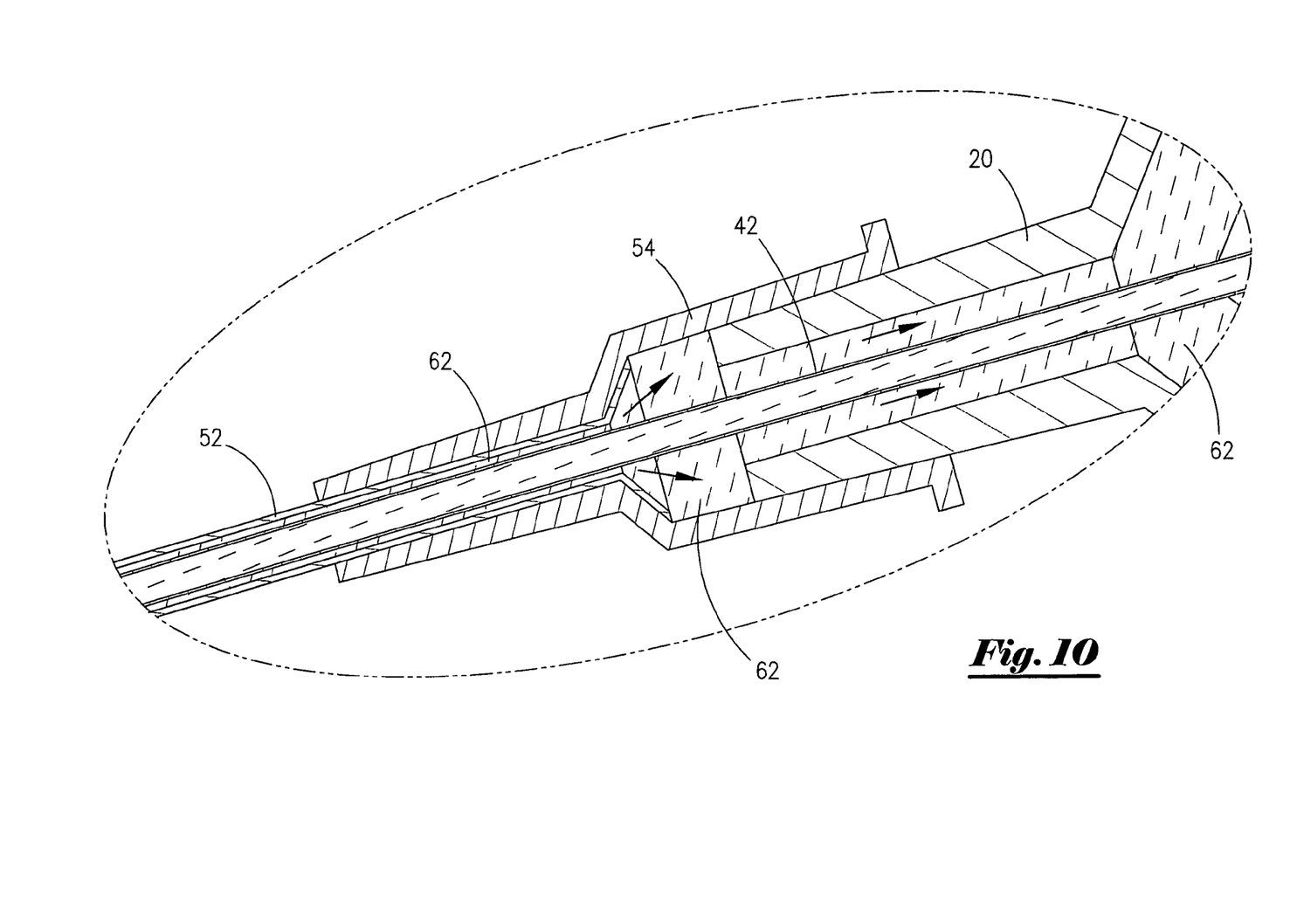
FIG. 10 is an enlarged cross-section view of area 10 seen in FIG. 9.
Figure 11:
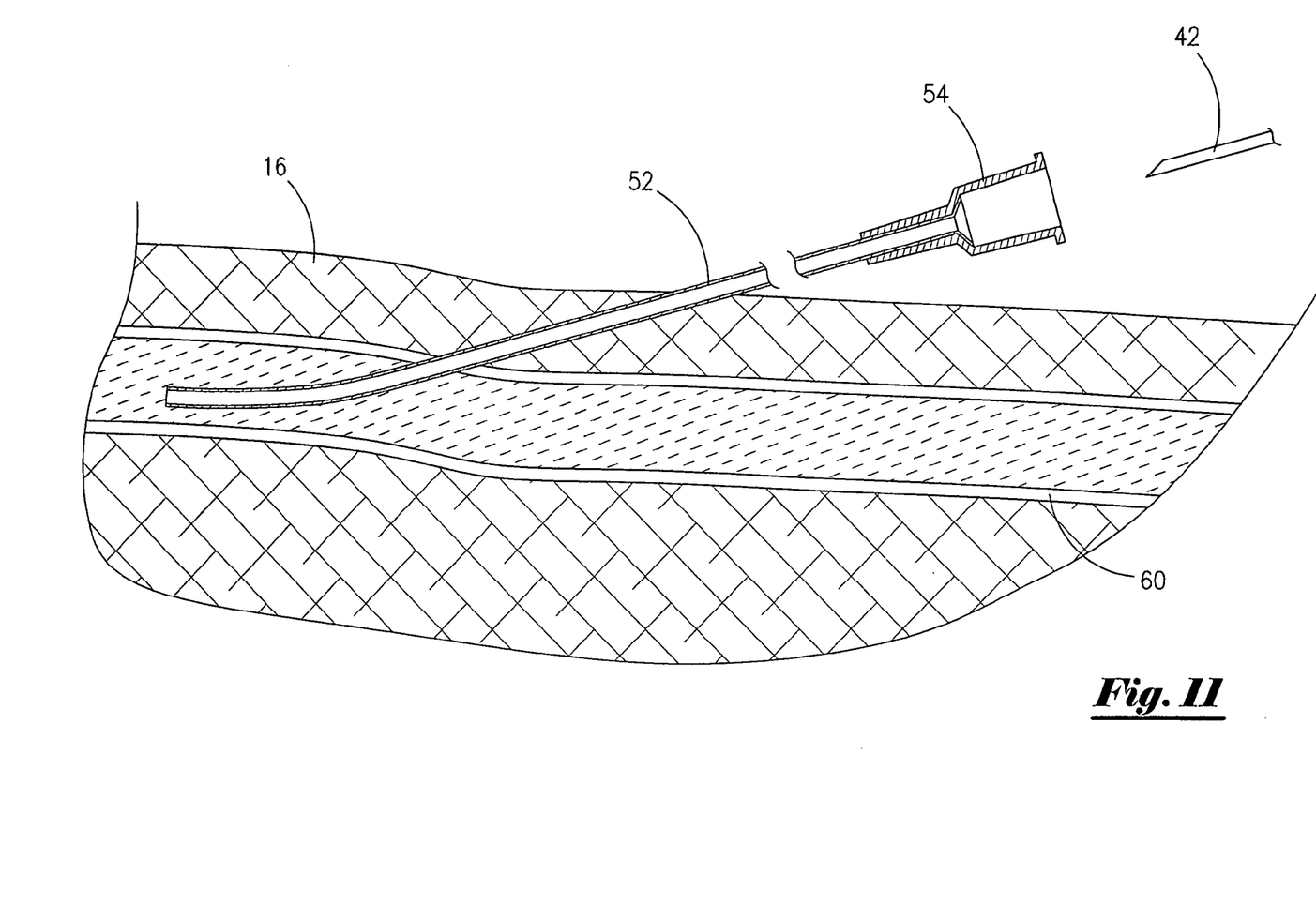
FIG. 11 is a cross-section view of the subcutaneous blood vessel showing proper insertion of the catheter assembly.
Figure 12:
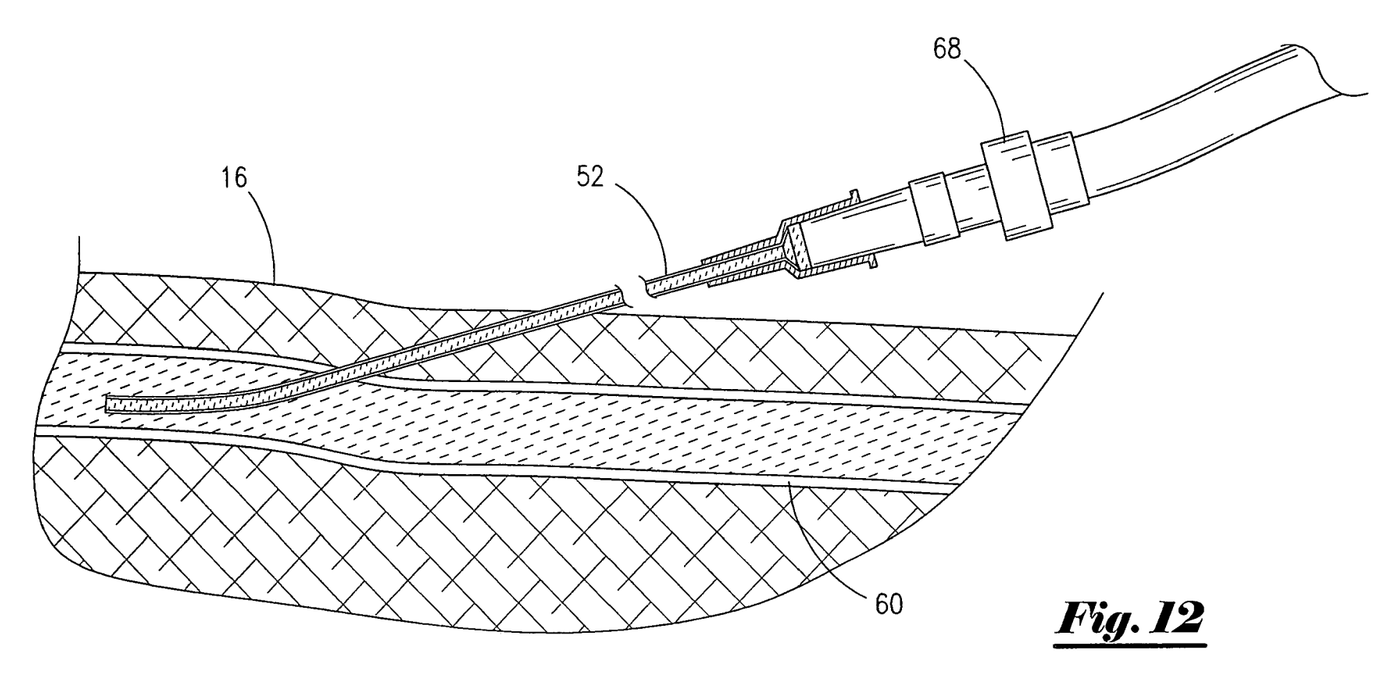
FIG. 12 is a partial cross-section of the subcutaneous blood vessel showing catheter assembly and tubing coupling attached.

In use, as shown in FIG. 6, we see the catheter assembly 14 is fitted to the insertion assembly 12 by threading the needle 42 through the cannula 52. It should be noted that the cannula 52 is slightly shorter than the needle 42 so as to allow the needle to puncture the skin and blood vessel 60 prior to entry of the cannula 52. As the needle 42 punctures the blood vessel 60, as seen in FIG. 8, pressure within the blood vessel 60 forces blood 62 through the needle 42 and into the transparent void or chamber space 32 located within the plunger assembly 26 thereby providing a visual indication of the presence of arterial pressurized blood 62. Without moving the catheter assembly 14 or the insertion assembly 12 the practitioner displaces the plunger assembly 26 via the knob 28 a short distance within the transparent sleeve 18, thereby withdrawing the needle 42 a short distance within the cannula and thereby producing a negative pressure void 64 between the conical portion 34 and the nipple portion 20 of the transparent sleeve 18, as seen in FIG. 9. If, the cannula 52 is positioned properly within the blood vessel 60 the negative pressure within the void 64 allows blood 62 to pass between the cannula 52 and the needle 42 and appear in the hub 54 and void 64, thereby providing a visual indication that the cannula 52 is located within the lumen of the blood vessel 60, as seen in FIG. 10. If no blood 62 appears in the transparent hub 32 and void 64 the cannula 52 is not properly positioned within the blood vessel 60, in which case the practitioner may simply advance the entire insertion assembly 10 thus extending the cannula 52 further into the blood vessel 60. If blood still does not appear in the hub 54 there is chance that the needle has only nicked the blood vessel. The plunger assembly 26 may be advanced and the entire assembly repositioned so as to reacquire the blood vessel 60. When the blood vessel 60 is reacquired the previous steps are repeated. When blood 62 appears in the hub 54 and void 64, the cannula 52 is carefully threaded sufficiently into the lumen of the blood vessel 60, the insertion assembly 12 may be removed from the catheter hub 54, as shown in FIG. 11. At this time, tubing coupling 68, or other such devices used to prevent further bleeding through the open port of hub 54, as shown in FIG. 12, may be attached to the hub 54.

Since the needle 42 is attached to the plunger assembly 26 and blood is present in the chamber 32 when being removed from the catheter assembly 14, care should be taken in disposing of the entire insertion assembly 12.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

What is claimed is:

1. A catheter insertion assembly comprising:
   a) a transparent tubular member open at each end;
   b) a plunger assembly slidable within said tubular member having a stem portion at a first end;
   c) an at least a partially transparent chamber attached to said stem portion having a needle base and sealing member on a second end of the plunger assembly;
   d) an elongated tubular needle embedded within said needle base and extending there from with said needle in fluid communication with said transparent chamber;
   e) a catheter assembly, a cannula and a transparent hub attached to said second end with said tubular needle passing longitudinally through said cannula; and
   f) a fluid passage formed between said needle and said cannula so that when the plunger is retracted a vacuum is established within the fluid passage and blood is drawn through the fluid passage into the transparent hub within the tubular member so that a user can identify blood flow within the transparent hub of the catheter assembly.

2. The catheter insertion assembly according to claim 1 wherein said transparent tubular member further comprises external upper and lower flat areas and concave external side walls for gripping said tubular member.

3. The catheter insertion assembly according to claim 1 wherein said transparent chamber is vented to atmosphere through said stem portion.

4. The catheter insertion assembly according to claim 1 wherein said tubular needle is threaded though a lumen of said cannula.

5. The catheter insertion assembly according to claim 1 wherein said sealing member provides a sliding seal between said plunger assembly and said transparent tubular member.

6. The catheter insertion assembly according to claim 1 wherein displacement of said plunger within said transparent tubular member defines a void between said tubular member and said needle base.

7. The catheter insertion assembly according to claim 1 wherein said plunger assembly is rotationally oriented relative to said transparent tubular member.

8. A catheter insertion assembly comprising:
   a) a transparent tubular member open at each end with one mammilated end;
   b) a plunger assembly slidable within said tubular member having a stem portion with a knob at one end;
   c) a transparent chamber attached to said stem portion opposite said knob having a needle base and sealing member;
   d) an elongated tubular needle having a chamfer at one end embedded within said needle base and extending there from with said needle in fluid communication with said transparent chamber;
   e) a catheter assembly, a cannula and a hub attached to said mammilated end with said tubular needle passing longitudinally through said cannula; and
   f) a fluid passage formed between said needle and said cannula for allowing blood flow through the fluid passage into the transparent hub as a vacuum is established within the fluid passage when the plunger is retracted within the tubular member so that a user can verify that the cannula has entered the blood vessel by identifying blood flow within the transparent hub of the catheter assembly.

9. The catheter insertion assembly according to claim 8 wherein said sealing member is in sliding contact with interior of said transparent tubular member.

10. The catheter insertion assembly according to claim 9 wherein neutral position for said plunger is with said needle base in contact with said mammilated end.

11. The catheter insertion assembly according to claim 10 wherein displacement of said plunger from said neutral position retracts said tubular needle to within said cannula and defines a void between said seal and said mammilated end.

12. The catheter insertion assembly according to claim 10 wherein said transparent chamber is vented through said stem portion.

13. The catheter insertion assembly according to claim 8 wherein said stem portion comprises a step portion adjacent said knob for rotationally orienting said plunger assembly relative to said transparent tubular member.

14. The catheter insertion assembly according to claim 13 wherein said transparent tubular member is notched to receive said step portion for rotationally orienting said chamfer relative to said plunger assembly.

15. A catheter insertion apparatus comprising:
 a) a transparent tubular member open at each end with one mammilated end;
 b) a seal assembly having a stem portion slidable within said transparent tubular member and a knob at one end located external of said transparent tubular member;
 c) an elongated tubular needle having a proximate end and a distal end said proximate end attached to said seal assembly said distal end having a chamfer;
 d) a transparent chamber in fluid communication with said tubular needle; wherein the transparent chamber is attached to said stem portion of the seal assembly opposite an end of said knob;
 e) a cannula extending from said mammilated end with said tubular needle passing longitudinally through said cannula; and
 f) a fluid passage formed between said needle and said cannula for drawing blood flow through the fluid passage into the transparent hub when a vacuum is established within the fluid passage as the plunger is retracted within the tubular member so that a user can verify blood flow within the cannula from the blood flow into the transparent hub of the catheter assembly.

16. A method for inserting a catheter assembly having a cannula and transparent hub comprising the steps of
 a) providing an apparatus comprising:
  i) a transparent tubular member open at each end with one mammilated end;
  ii) a plunger assembly slidable within said tubular member having a stem portion;
  iii) a transparent chamber attached to said stem portion having a needle base and sealing member; and
  iv) an elongated tubular needle having a chamfer at one end embedded within said
 needle base and extending there from with said needle in fluid communication with said transparent chamber;
 b) threading said tubular needle longitudinally through said mammilated end and said hub and cannula;
 c) attaching said hub portion to said mammilated end;
 d) inserting said catheter and tubular needle into a subcutaneous blood vessel thereby allowing pressurized blood to flow into said transparent chamber; and
 e) displacing said plunger thereby defining a void between said sealing member and said mammilated end and thus producing a negative pressure within said void allowing blood to be drawn between said needle and cannula and into said transparent hub so that a user can identify blood flow within the transparent hub of the catheter assembly.

17. A method for inserting a catheter comprising the steps of:
 a) providing a catheter assembly comprising:
  i) a transparent tubular member open at each end with one mammilated end;
  ii) a plunger assembly slidable within said tubular member having a stem portion;
  iii) a transparent chamber attached to said stem portion having a needle base and sealing member;
  iv) an elongated tubular needle having a chamfer at one end embedded within said needle base and extending there from with said needle in fluid communication with said transparent chamber;
  v) a transparent hub member attached externally to said mammilated end having
 an elongated cannula threaded longitudinally over said tubular needle to a point adjacent said chamfer;
 b) inserting said catheter and tubular needle into a subcutaneous blood vessel hereby allowing pressurized blood to flow into said transparent chamber; and
 c) displacing said plunger thereby defining a void between said sealing member and said mammilated end and thus producing a negative pressure within said void allowing blood to be drawn between said needle and cannula and into said transparent hub so that a user can identify blood flow within the transparent hub of the catheter assembly.

18. A catheter insertion assembly comprising:
 a) a tubular member open at each end;
 b) a plunger assembly slidable within said tubular member having a stem portion at a first end;
 c) an at least partially transparent chamber attached to said stem portion having a needle base and sealing member on a second end of the plunger assembly;
 d) an elongated tubular needle embedded within said needle base and extending there from with said needle in fluid communication with said partially transparent chamber;
 e) a catheter assembly, a cannula and a transparent hub attached to said second end with said tubular needle passing longitudinally through said cannula; and
 f) a fluid passage formed between said needle and said cannula for drawing blood flow through the fluid passage into the transparent hub when a vacuum is established within the fluid passage as the plunger is retracted within the tubular member so that a user can identify blood flow transparent hub of the catheter assembly to verify blood flow through the cannula.

\* \* \* \* \*